United States Patent
Banes (10) Patent No.: US 6,586,235 B1
(45) Date of Patent: Jul. 1, 2003

(54) APPARATUS FOR GROWING CELLS IN CULTURE UNDER SHEAR STRESS AND/OR STRAIN

(75) Inventor: Albert J. Banes, Hillsborough, NC (US)

(73) Assignee: Flexcell International Corporation, McKeesport, PA (US)

( * ) Notice: Subject to any disclaimer, the term of this patent is extended or adjusted under 35 U.S.C. 154(b) by 0 days.

(21) Appl. No.: 09/454,327

(22) Filed: Dec. 3, 1999

Related U.S. Application Data
(60) Provisional application No. 60/111,023, filed on Dec. 4, 1998.

(51) Int. Cl.$^7$ ................................................. C12M 3/00
(52) U.S. Cl. .................. 435/293.1; 435/297.2; 435/297.5; 435/305.3; 435/305.4
(58) Field of Search ............... 435/287.1, 293.2, 435/289.1, 305.1, 305.2, 305.3, 305.4, 288.3, 288.4, 297.2, 297.5

(56) References Cited

U.S. PATENT DOCUMENTS

| | | | |
|---|---|---|---|
| 4,087,327 A | 5/1978 | Feder et al. | 195/1.7 |
| 4,623,355 A | 11/1986 | Sawruk | 623/66 |
| 4,642,220 A | 2/1987 | Bjorkman | 422/101 |
| 4,695,547 A | 9/1987 | Hilliard et al. | 435/173 |
| 4,831,869 A * | 5/1989 | Fowler et al. | |
| 4,839,280 A | 6/1989 | Banes | 435/285 |
| 4,839,292 A | 6/1989 | Cremonese | 435/313 |
| 4,908,319 A * | 3/1990 | Smyczek et al. | |
| 4,940,853 A | 7/1990 | Vandenburgh | 435/240.23 |
| 4,974,952 A * | 12/1990 | Focht | 356/246 |
| 5,273,905 A * | 12/1993 | Muller et al. | |
| 5,348,879 A | 9/1994 | Shapiro et al. | 435/240.241 |
| 5,414,556 A * | 5/1995 | Focht | |
| 5,460,945 A * | 10/1995 | Springer et al. | |
| 5,496,697 A * | 3/1996 | Parce et al. | |
| 5,843,766 A * | 12/1998 | Applegate et al. | |
| 5,958,760 A * | 9/1999 | Freeman | |

FOREIGN PATENT DOCUMENTS

| | | | |
|---|---|---|---|
| GB | 2155948 | 10/1985 | ............ C12M/1/18 |

OTHER PUBLICATIONS

Baxter et al. 'Configurations of a Flow Injection System for Perfusion Studies of Adherent Cells'. Anal. Chem. vol. 67 (1995) pp. 1486–1490.*

Fredrickson et al. 'Shear–Dependent Rolling . . . '. Blood. vol. 92 (Nov. 1998), No. 10, pp. 3684–3693.*

Grabowski. 'Effects of Contrast Media on Endothelial Cell Monolayers Under Controlled Flow Conditions.' The American Journal of Cardiology. vol. 64 (Sep. 1989), pp. 10E–15E.*

Sirois et al. 'Endothelial cells exposed to erythrocytes under shear stress; An in vitro study'. Biomaterials. vol. 19 (1988), pp. 1925–1934.*

Grabowski et al. 'Prostacyclin production by cultured endothelial cell monolayers exposed to step increases in shear stress'. J. Lab. Clin. Med. vol. 105 (Jan. 1985), No. 1, pp. 36–43.*

Leung et al., "Cyclic Stretching Stimulates Synthesis of Matrix Components by Arterial Smooth Muscle Cells in vitro", Science, vol. 191, Feb. 6, 1976, pp. 475–477.

Brunette, "Mechanical Stretching Increases the Number of Epithelial Cells Synthesizing DNA in Culture", J. Cell Sci. 69, 35–45 (1984).

(List continued on next page.)

*Primary Examiner*—William H. Beisner
(74) *Attorney, Agent, or Firm*—Webb Ziesenheim Logsdon Orkin & Hanson, P.C.

(57) ABSTRACT

A cell culture device for inducing shear stress and on substrate strain on cells. The device includes a cell culture membrane and a flow pathway for moving fluid across cells growing on the membrane to apply shear stress on the cells.

19 Claims, 10 Drawing Sheets

OTHER PUBLICATIONS

Somjen et al., "Bone Remodelling Induced by Physical Stress is Prostaglandin $E_2$ Mediated", Biochimica et Biophysica Acta, 627 (1980) 91–100.

Banes et al., "A New Vacuum–Operated Stress–Providing Instrument That Applies Static or Variable Duration Cyclic Tension or Compression to Cells In Vitro", J. Cell Sci. 75 (1985) pp. 1–8.

Leung et al., "A new In Vitro System for Studying Cell Response to Mechanical Stimulation", Exp. Cell Res. 109 (1977), pp. 285–298.

Winston et al., "The In Vitro Response of Endothelium to Mechanical Loading", 38th ACEMB (1985), p. 88.

Winston et al., "Response of Endothelial Cells in Cluture to Biaxial Deformation", Northeast Bioengineering Conference, University of Pittsburgh, (1987), 2 pp.

Thibault et al., "Mechanical Characterization of Membrane-like Biological Tissue", J. Biomechanical Engr., (1982), pp. 1–8.

* cited by examiner

APPARATUS FOR GROWING CELLS IN CULTURE UNDER SHEAR STRESS AND/OR STRAIN

RELATED APPLICATION

This application claims the benefit of U.S. Provisional Patent Application Serial No. 60/111,023, filed Dec. 4, 1998, entitled "Apparatus for Growing Cells in Culture Under Shear Stress and/or Strain."

BACKGROUND OF THE INVENTION

1. Field of the Invention

The present invention is directed toward a cell culture assembly used in the biomedical science field of tissue engineering and, more specifically, to a cell culture assembly through which fluid may flow for applying deformations to cells that include fluid-induced stress or substrate-induced strain to cultured cells.

2. Prior Art

In the human body, many cells are constantly subjected to stress from fluid flow. Fluid flow in the body includes blood flow through the vasculature, lymph in the lymphatics, cerebrospinal fluid flow, any secretion in ducts, and also the movement of interstitial fluid in the matrix between and among cells in any tissue. Stressing cells in culture simulates the in vivo environment, causing dramatic morphologic changes and biomechanical responses in the cells. There are both long and short-term changes that occur when cells are stressed in culture, such as alterations in the rate and amount of protein expression and secretion, the rate of cell division and alignment, changes in energy metabolism, changes in rates of macromolecular synthesis or degradation, and other changes in biochemistry and bioenergetics. Prior devices have been developed for applying substrate deformation on cells and applying fluid-induced shear stress by subjecting the cells to fluid flow. However, none of these devices have allowed for alternating or simultaneous application of both types of mechanical loading of cells in vitro and for quantitation of the applied stresses and strains.

A need remains for a cell culture assembly in which cells may be cultured and subjected to fluid-induced shear stress which is precisely controlled.

SUMMARY OF THE INVENTION

Accordingly, I have developed a cell culture assembly including a body having a flow surface extending across an upper surface of the body. The top surface of the body may also be used as a flow surface on which cells may be cultured. Moreover, a flexible membrane may be clamped by the body and also be used as a flow surface on which cells may be cultured. This rubber membrane may also be deformed by vacuum so this cell receives substrate tension in unconstrained distension may be deformed by stretching across a planar faced post so that the flexible substrate is deformed equibiaxially. Positive pressure may also be applied to deform the flexible membrane upward to apply a compressive deformation to overlying cells cultured on the top member. Both fluid stress and substrate strain may also be delivered simultaneously as often occurs in blood vessels or in other tissues.

The body further defines a passageway in fluid communication with the flow surface and a cover member covering the flow surface. The flow surface of the body and the cover member thereby define a flow chamber through which fluid may flow. A cell culture surface is positioned on the flow surface or on the cover or both. Cells cultured on the cell culture surface are subject to shear stress when fluid flows through the passageway and the flow chamber.

In one embodiment of the invention, the body has an upper surface defining a first opening therethrough. The assembly further includes a base attached to the body and a cell culture membrane fixed between the base and the body whereby the membrane covers the first opening, such that when fluid flows through the body passageway, the fluid passes across the membrane thereby inducing shear stress on cells growing on the membrane. The body passageway includes a pair of bores defined in the body on opposing sides of the first opening, wherein each bore extends between a side of the body and the upper surface. The upper surface defines a pair of second openings, preferably in the form of slits, on opposing sides of the first opening and each second opening is in fluid communication with one of the bores. A gasket is positioned on the body upper surface and surrounds the first opening and the second openings. The gasket is configured to retain fluid flowing out of one of the second openings and into the other second opening. A port is defined in the body for connection to a pressure supply. The body upper surface further defines an annular channel in fluid communication with the port. The gasket overlies the channel and the cover overlies the gasket. The gasket defines a plurality of holes which overlie the annular channel such that the cover seats on the gasket when negative pressure is applied to the port. Alternatively, the upper surface may be clamped by overlying pressure to the gasket and body by conventional assemblies such as a plate and fasteners.

The base comprises an annular member defining a chamber and having a wall with a top surface on which the membrane is seated. An insert is received within the chamber. The insert includes a support member with a support surface for supporting a portion of the membrane. The wall of the base defines an aperture and the insert defines an insert passageway extending between a side of the insert and the insert support surface where the insert passageway is in fluid communication with the aperture of the base wall. When negative pressure is applied to the chamber through the aperture, the membrane is urged against the insert support surface. Preferably, the insert includes a post spaced apart from the support member thereby defining an annular gap between the post and the support member. An opening defined in the support member is in fluid communication with the gap. Preferably, an upper surface of the post is lower than the support surface and an upper surface of the portion of the membrane supported by the support surface is in a plane of the upper surface of the body.

In another embodiment of the invention, the body includes a flow member and a pair of end members attached to opposing ends of the flow member, where the opposing ends of the flow member each define a recess, and where each flow surface extends between the recesses in the ends of the flow member. In this arrangement, the openings are defined in the end members and are in fluid communication with the recesses. An annular channel is defined in an upper surface of the body and surrounds the flow surface. The body defines a port in fluid communication with the channel whereby when negative pressure is applied to the port, the cover is urged toward the body. A gasket defining an opening aligned with the flow surface and defining a plurality of holes therethrough is positioned between the body and the cover. The gasket opening overlies the flow surface and the holes overlie the channel, such that when negative pressure is applied to the port, the cover sealingly seats on the gasket and the gasket sealingly seats on the body. The flow chamber is defined by the gasket, the cover and the recess. The body may include a plurality of flow surfaces with the channel surrounding each flow surface defined in the body, and the gasket defining a plurality of openings each overlying a flow surface. Each end of the body then defines a plurality of openings aligned with each of the flow surfaces.

DESCRIPTION OF THE DRAWINGS

A complete understanding of the invention will be obtained from the following description when taken in connection with the accompanying drawing figures wherein like reference characters identify like parts throughout.

DETAILED DESCRIPTION OF THE PREFERRED EMBODIMENTS

For purposes of the description hereinafter, the terms "upper", "lower", "right", "left", "vertical", "horizontal", "top", "bottom" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present invention includes a cell culture assembly for applying shear stress to cells. One embodiment of the invention is the cell culture assembly 2 shown in FIGS. 1 and 2 which includes a body 10 through which fluid may flow. The body 10 shown in detail in FIGS. 2–5 includes an upper surface 12 which defines a central opening 14 surrounding a rim 15 centrally located in a central planar portion 16 of the upper surface 12. The opening 14 and rim 15 are preferably rectangular in shape. The planar portion 16 is disposed between a pair of integrally formed housings 17. Preferably, the body 10 is formed from aluminum, but stainless steel, lucite or other like materials may be used in the fabrication.

Figure 4:
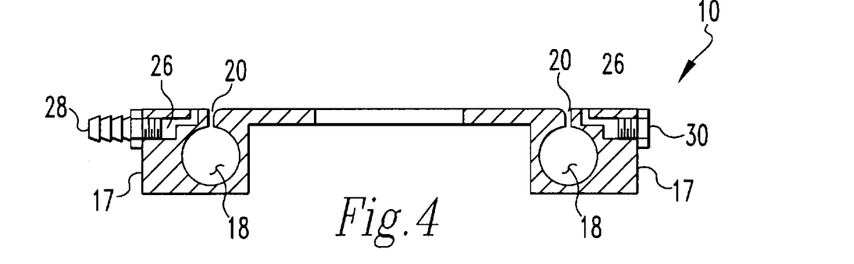
FIG. 4 is a partial sectional view of the body taken along lines IV—IV in FIG. 3.
Figure 5:
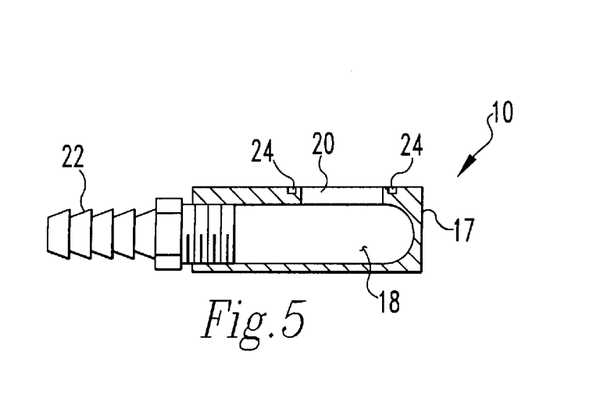
FIG. 5 is a partial sectional view of the body taken along lines V—V in FIG. 3.

Referring to FIGS. 4 and 5, a bore 18 is defined in each of the housings 17 on opposing ends of the body 10. Each bore 18 is in fluid communication with a slit 20 defined in the upper surface 12. The bores 18 are each preferably internally threaded to accept a fitting 22. The fittings 22 may constitute quick disconnect valves instead of the particular fitting shown in FIGS. 3 and 5. Also defined in the upper surface 12 is a continuous channel 24, preferably having a rectangular configuration. The channel 24 surrounds the central opening 14 and the slits 20. The shorter sides of the rectangular channel 24 are each in fluid communication with a vacuum opening 26 defined in each of the ends of the body 10. The vacuum openings 26 in the ends of the body are preferably internally threaded to accept a vacuum fitting 28 at one end and a sealing nut 30 at the other end. Either end of the body 10 may accept either of the vacuum fitting 28 or the nut 30.

Figure 1:
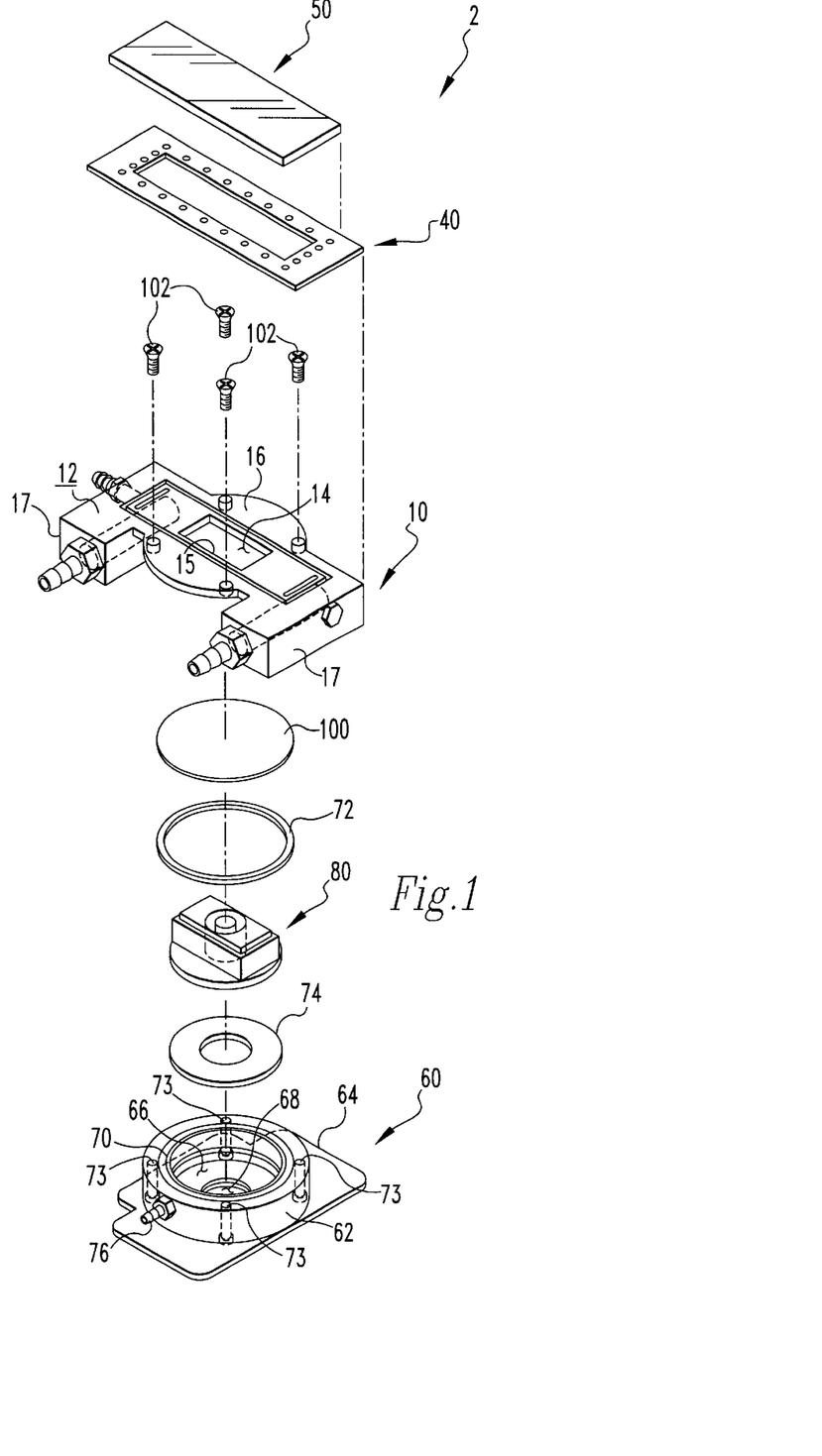
FIG. 1 is an exploded perspective view of a cell culture assembly made in accordance with the present invention including a body, an insert and a base.
Figure 2:
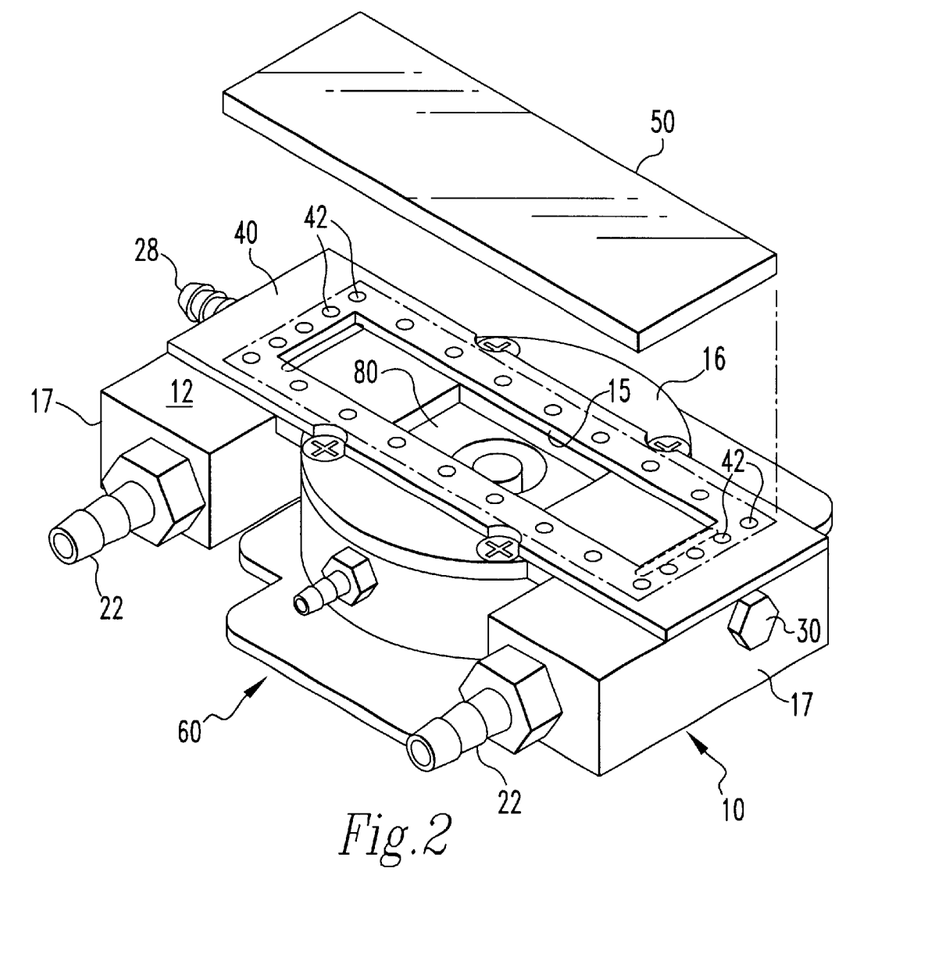
FIG. 2 illustrates a perspective view of the cell culture assembly depicted in FIG. 1, partially assembled.
Figure 3:
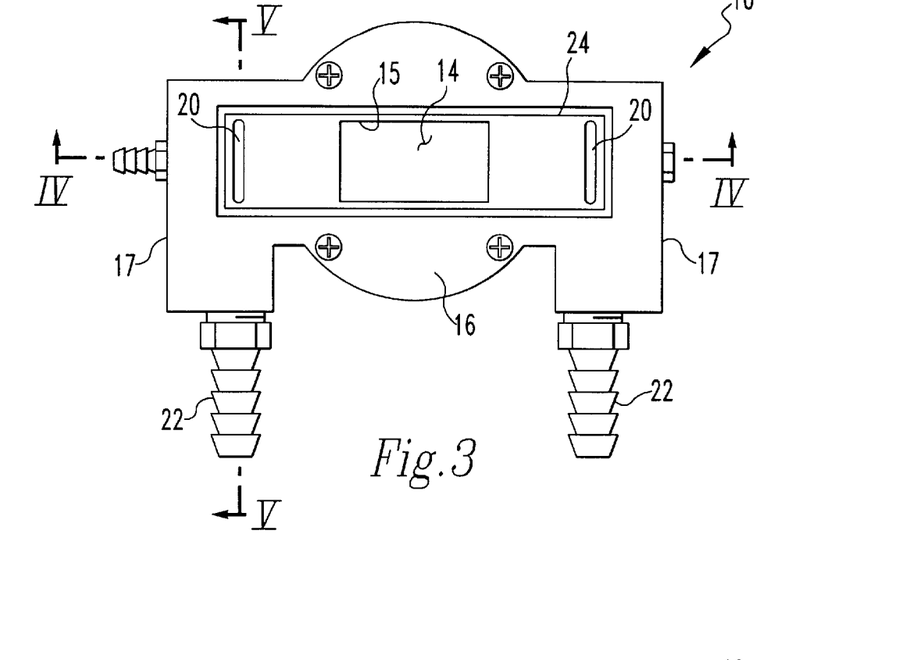
FIG. 3 is a plan view of the body shown in FIG. 1.

Referring to FIGS. 1 and 2, overlying the body 10 is a gasket 40, preferably having a configuration which coordinates with the configuration of the channel 24. The gasket 40 shown in FIGS. 1 and 2 is rectangular in shape so that the gasket 40 covers the channel 24 while leaving exposed the slits 20 and the central opening 14. The gasket 40 is preferably formed from a silicone rubber and includes a two-sided acrylic-silicone mastic (not shown) adhered to one side. The silicone side of the mastic is adhered to the gasket 40 and the acrylic side is adhered to the upper surface 12 of the body 10. A plurality of apertures 42 is defined in the gasket 40 at locations whereby the apertures 42 are in overlying relation to the channel 24 defined in the upper surface 12 of the body 10. The gasket 40 is shown in FIG. 2 as covering a portion of the upper surface 12. However, the gasket may completely cover the entire upper surface 12 to enhance the seal formed thereby. A cover 50 such as a glass microscope slide is positioned over the gasket 40. Upon application of a vacuum through one of the vacuum openings 26 in an end of the body 10 via the vacuum fitting 28, air is drawn through the apertures 42 in the gasket 40, through the channel 24 in the upper surface 12 and out through the vacuum opening 26 in the side of the body 10 and through the vacuum fitting 28. This causes the cover 50 to be pulled down in sealing engagement with the gasket 40.

Alternatively, the cover 50 may be clamped to the gasket 40 and body 10. Conventional clamping assemblies may be used to clamp the cover 50 to the gasket 40 and the body 10.

The cell culture assembly 2 further includes a base 60 as disclosed in co-pending U.S. application Ser. No. 09/201,570, now U.S. Pat. No. 5,048,723, entitled "Culture Plate for Applying Mechanical Load to Cell Cultures," incorporated herein by reference. The body 60 has a wall 62, preferably cylindrical in configuration, extending from a planar member 64 and defining a cylindrical well 66. The planar member 64 defines a base opening 68 having a diameter which preferably is smaller than an inner diameter of the well 66. The planar member 64 preferably is sized and configured for placement on the objective of a microscope. A groove 70 is defined in a top surface of the wall 62 and is sized to accept an O-ring 72. The top surface of the wall 62 also defines a plurality of threaded holes 73 used in assembling the assembly 2 as described below. A spacer 74 preferably formed from silicone in a ring shape is positioned within the well 66 on the planar member 64. A pressure differential supply fitting 76 extends outwardly from the wall 62 and communicates with the well 66 via an opening through the wall 62. An insert 80 (described in detail below) is received within the well 66 and seats on the spacer 74.

A flexible cell culture membrane 100 is disposed between the body 10 and the base 60. The body 10 clamps the membrane 100 and the O-ring 72 against the top surface of the wall 62 using conventional means such as a plurality of screws 102 threaded through a perimeter of the body planar portion 16 and into the threaded holes 73 in the base 60. A portion of the membrane 100 is exposed through the central opening 14. Cells are culturable on the exposed portion of the membrane 100. Alternatively, cells may be cultured on the cover 50. The integrity of a seal formed between the body 10, the membrane 100 and the base 60, thereby forming a flow chamber, is in part achieved by use of the insert 80 as described below.

Figure 6:
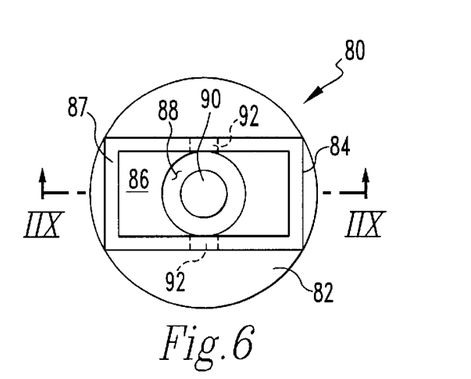
FIG. 6 is a plan view of the insert shown in FIG. 1.
Figure 7:
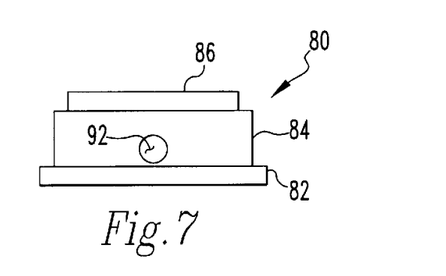
FIG. 7 is a side view of the insert shown in FIG. 6.
Figure 8:
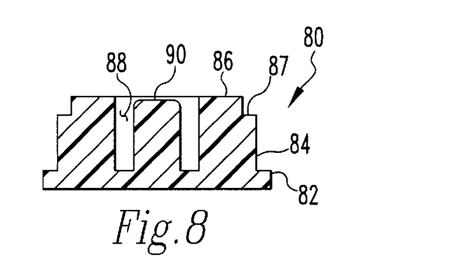
FIG. 8 is a cross-sectional view of the insert taken along lines VIII—VIII shown in FIG. 6.

The insert 80 shown in FIG. 1 is shown in detail in FIGS. 6–8. The insert 80 includes a planar member 82 and a support member 84 bearing a support surface 86 extending therefrom. The support member 84 includes a ledge 87. The ledge 87 is sized to accept and mate with the rim 15 of the planar portion 16 surrounding the central opening 14. In this manner, the membrane 100 is clamped between the rim 15 of the body 10 and the ledge 87 of the insert 80. The support member 84 defines an annular opening 88 surrounding a post 90. As may be seen in FIG. 8, an upper surface of the post 90 is lower than the support surface 86. A layer of lubricating material (not shown), such as silicone, may be positioned on the top of the post 90 such that the support surface 86 and surface of the lubricating material are in a common plane. A passageway 92 is defined in each of two opposing sides of the support member 84 with each passageway 92 being in fluid communication with the annular opening 88. The post 90 may be one of a variety of geometrical shapes such as conical or frustoconical or have a constant rectangular or square cross-sectional configuration.

In operation, when a pressure differential, e.g., negative pressure, is applied to the pressure differential supply fitting 76, air is drawn from the annular opening 88 through the passageways 92 and out the pressure differential supply fitting 76 so that the membrane 100 is urged downwardly over or upwardly above the support surface 86 and over the lubricating material covering the post 90. Negative pressure is also applied to the vacuum fitting 28 on the body 10 to pull the cover 50 against the gasket 40 seated on the body 10. Upon application of negative pressure to the base 60 and the body 10, fluid at a selected flow rate is directed into one of the fittings 22, through the corresponding bore 18, up through the corresponding slit 20, across the membrane 100 covering the central opening 14 and out through the opposing slit 20, the other bore 18 and the other fitting 22. The membrane 100 preferably extends through the central opening 14 in the body 10 so that the fluid flows smoothly across one portion of the upper surface 12 on one side of the central opening 14, over cells growing on the membrane 100 and across the other portion of the upper surface 12. In this manner, the amount of flow to induce stress on cells growing on the membrane 100 from fluid flow thereover may be altered and studied. The flow rate of fluid passing through the body 10 can be controlled and the shear stress on cells growing on the membrane 100 may be calculated. By varying the flow rate to the body 10, varying degrees of shear stress may be applied to cells. Hence, the impact of shear stress on the cells can be determined quantitatively. The membrane 100 preferably is formed from a transparent material so that the entire assembly may be placed on a microscope. The effect of fluid flow and stress therefrom on cells growing on the membrane 100 may be actively studied.

Although not shown in the drawings, the assembly 2 preferably includes a fluid pump, preferably a peristaltic pump, one or more fluid pulse dampeners, a digital flow meter, valves to regulate fluid sampling of flow to the assembly 2 and a fluid reservoir. All components are connected with flexible tubing in a continuous or discontinuous flow loop. The fluid flowing through the assembly 2 may be recycled therethrough in a continuous loop. In this manner, substances secreted by the cultured cells interact with the cells. Alternatively, the fluid may not be returned to the assembly 2 so that secreted substances do not effect the cells. The assembly 2 may further include a sampling port into the fluid effluent leaving the body 10. Fluid withdrawn can be biochemically analyzed.

Control of fluid flow is achieved by regulation of the pump flow rate, the bore size of the tubing and the opening and closing of a valve or valves positioned upstream of the flow chamber, downstream of the flow chamber or in both locations. Flow control may be achieved by regulation of the pump flow rate alone. The flow rate may range from picoliters to milliliters of total flow to continuous flow of fluid. Alternatively, the pump flow rate may be maintained at a constant rate and the valves may be opened and closed to direct fluid flow away from the flow chamber to provide rapid regulation of flow rate, particularly for rapid oscillations in the flow stream. Alternatively, the valves may be used to provide flow reversals to the flow chamber so that fluid enters the chamber from one direction at one instant then reverses direction and enters from the opposite side of the chamber at the next instant. These levels of flow control permits both continuous fluid flow, and discontinuous fluid flow, the latter as a pulsating flow or a flow reversal, as occurs in the vasculature, lymphatics and in interstitial fluid flow in tissues. The precise nature of the rate of fluid flow, and type of fluid flow may have unique consequences for the response(s) of the cells or tissue experiencing the deformation. This is particularly true when fluid flow is combined with substrate strain. This is an imperative point for cells that may be "conditioned" by this mechanical environment and transferred to a location in the body in a tissue engineering application where they must withstand the rigors of the mechanically active environment of the body.

Figure 9:
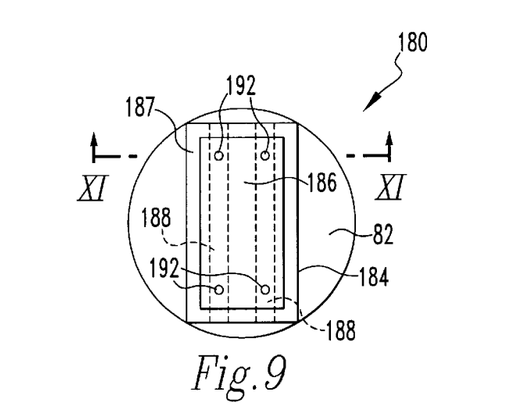
FIG. 9 is a plan view of an alternative insert made in accordance with the present invention.
Figure 10:
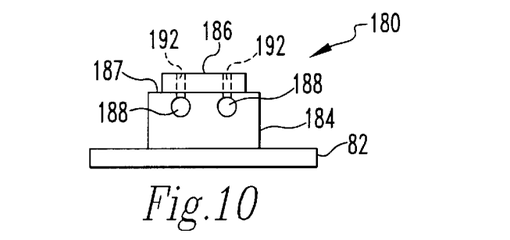
FIG. 10 is an end view of the insert shown in FIG. 9.
Figure 11:
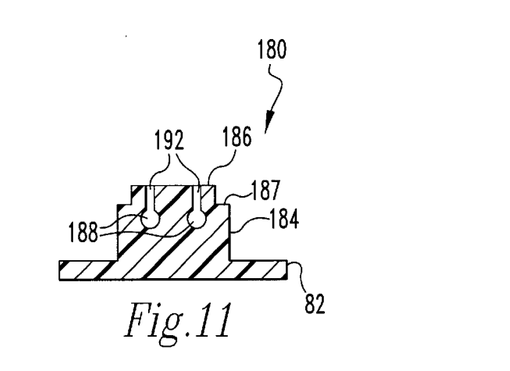
FIG. 11 is a cross-sectional view of the insert taken along lines XI—XI in FIG. 9.

FIGS. 9–11 show an alternative insert 180. The insert 180 includes a support member 184 extending from a planar member 82 and including a substantially planar support surface 186 and a ledge 187. The support surface 186 is preferably rectangular in configuration. A plurality of, preferably two, bores 188 extends longitudinally through the support member 184. A plurality of, preferably four, holes 192 is defined in the support surface 186 and communicates with the bores 188. When insert 180 is used instead of the insert 80 in the assembly 2, the membrane 100 is clamped between the rim 15 of the body 10 and the ledge 187 of the insert 180 thereby maintaining the membrane 100 flat across the support surface 186. Negative pressure applied to the fitting 76 pulls air through the holes 192 and out through the bores 188, the well 66 and the fitting 76. The insert 180 serves to ensure uniformity in the flatness of the membrane 100.

Figure 12:
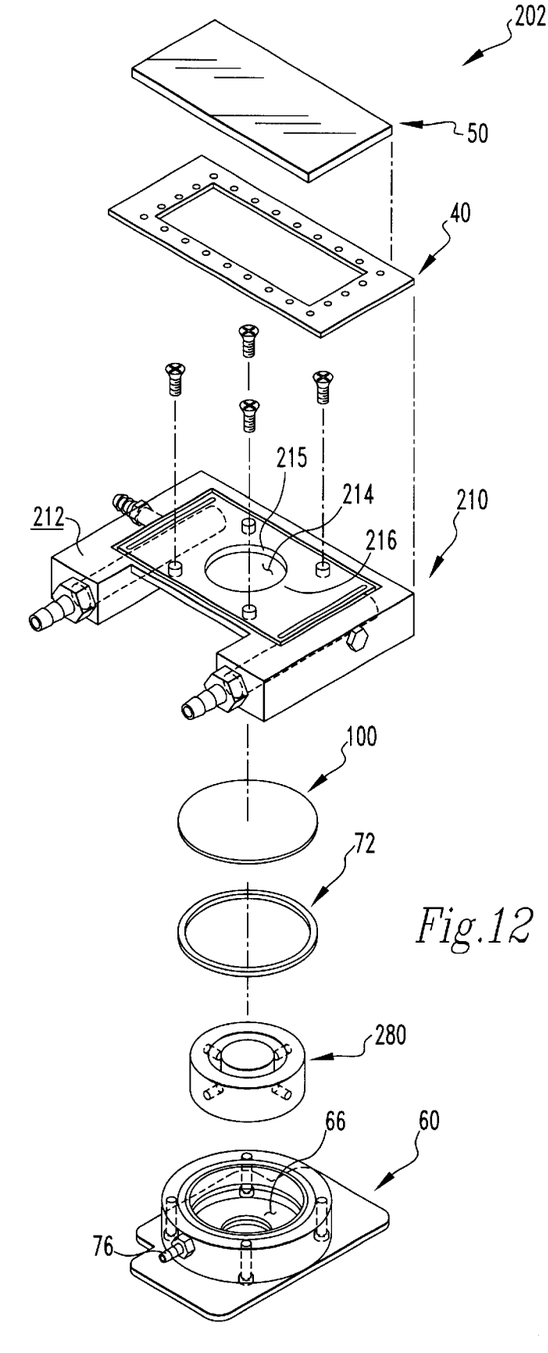
FIG. 12 is an exploded perspective view of another embodiment of a cell culture assembly made in accordance with the present invention including an insert.

Another embodiment of the invention is the cell culture assembly 202 shown in FIG. 12. The cell culture assembly 202 includes a cover 50, a gasket 40, a membrane 100, an O-ring 72 and a base 60 similar to those components described above in connection with assembly 2. However, assembly 202 includes a body 210 having an upper surface 212 which defines a central opening 214 surrounding a rim 215 which is preferably circular in configuration and centrally located in a central portion 216. All other components of the body 210 are similar to those of the body 10.

Figures 13, 14:
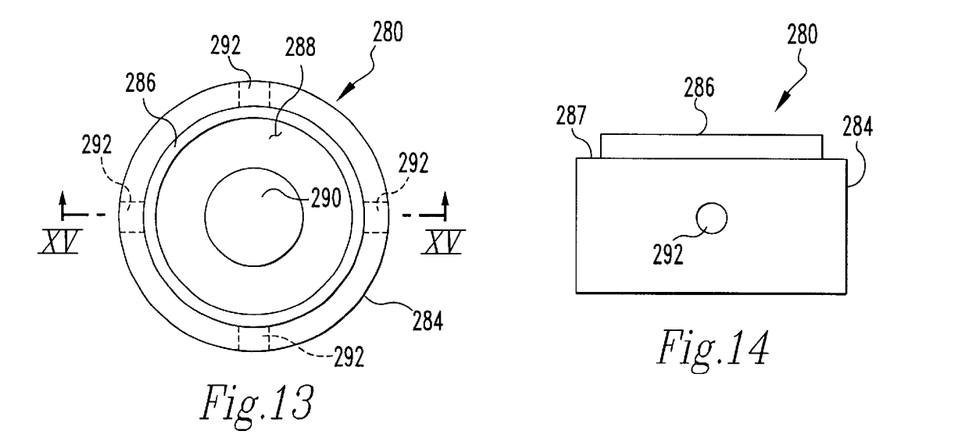
FIG. 13 is a plan view of the insert shown in FIG. 12.
FIG. 14 is a side view of the insert shown in FIG. 13.
Figure 15:
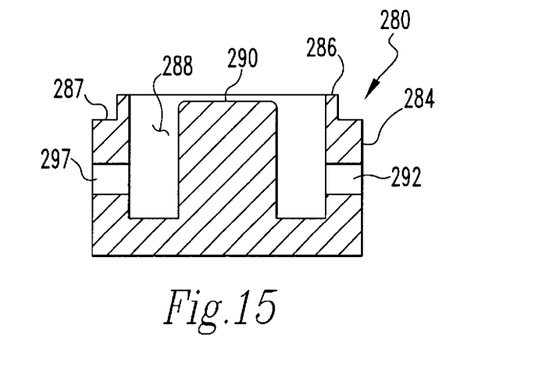
FIG. 15 is cross-sectional view of the insert taken along lines XV—XV in FIG. 13.

An insert 280 is received within the well 66. As shown in more detail in FIGS. 13–15, the insert 280 has a support member 284 with a preferably overall cylindrical shape. A ring-shaped support surface 286 stepped up from a ledge 287 supports the membrane 100 when the body 210 and the base 60 are clamped together with the membrane 100 therebetween. The ledge 287 is sized to accept and mate with the rim 215 of the body 210 surrounding the central opening 214. In this manner, the membrane 100 is clamped between the central portion 216 and the ledge 287. Cells may be cultured on the portion of the membrane 100 which is exposed through the central opening 214. The support member 284 defines an annular opening 288 surrounding a post 290. As can be best seen in FIG. 15, an upper surface of the post 290 is lower than the support surface 286. As is true for insert 80, a layer of lubricating material (not shown) may be placed on the top of the post 290 such that the support surface 286 and surface of the lubricating material are in a common plane. A plurality of, preferably four, holes 292 are defined in the support member 284 and communicate with the annular opening 288 and the well 66. When negative pressure is applied to the fitting 76, air is drawn from the annular opening 288 out through the holes 292, the well 66 and the fitting 76 to pull the membrane 100 against the support surface 186.

Yet another embodiment of the invention is shown in FIGS. 16–20. The cell culture assembly 302 shown in FIGS. 16 and 17 includes a preferably rectangular shaped body 310, a gasket 340 and a cover 350.

Figure 16:
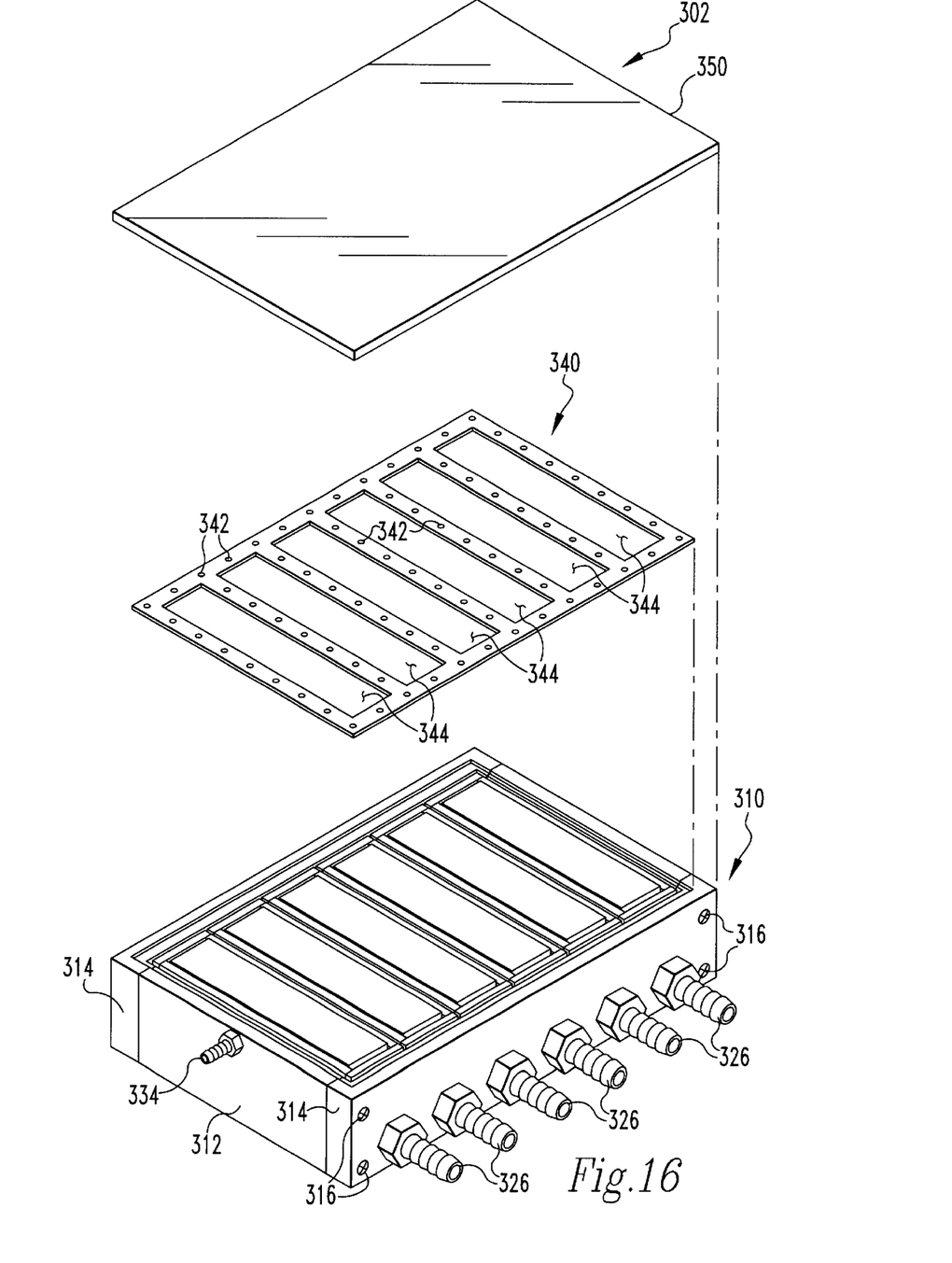
FIG. 16 is an exploded perspective view of another embodiment of the cell culture assembly made in accordance with the present invention including a cover, a gasket and a body.
Figure 17:
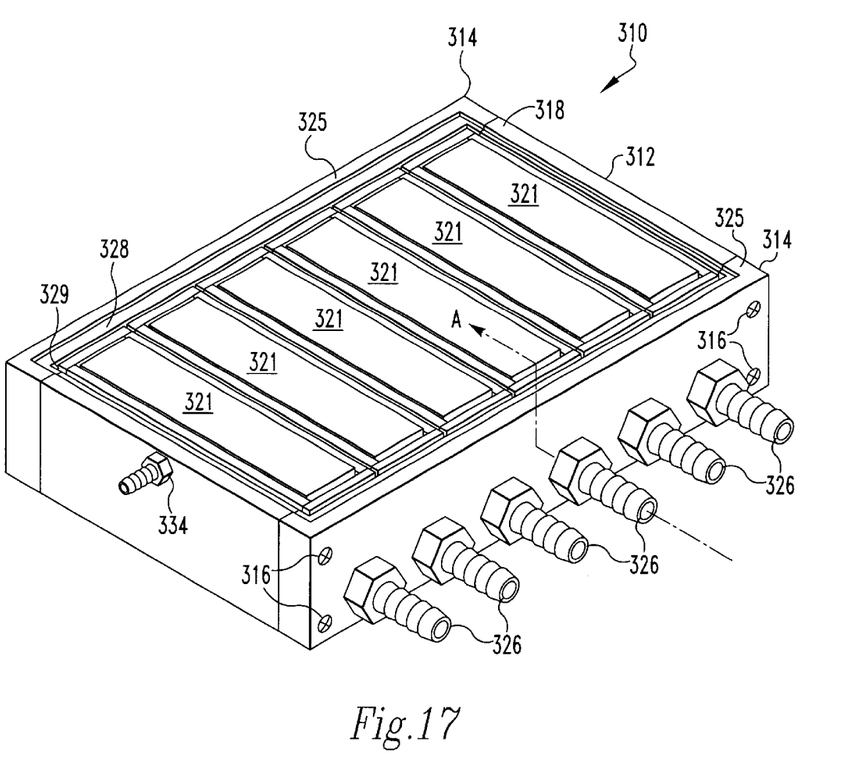
FIG. 17 is a perspective view of the body shown in FIG. 16.
Figure 18:
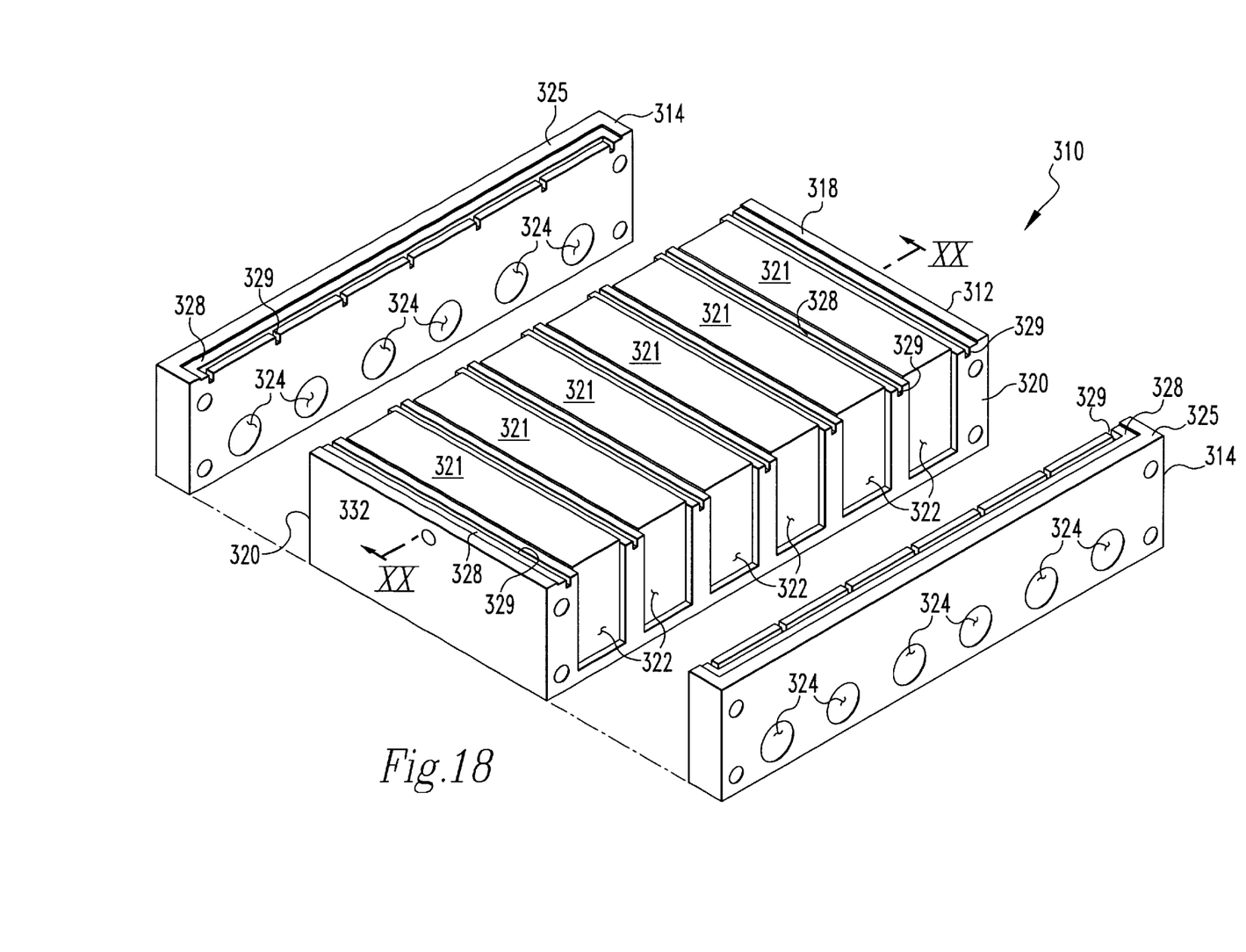
FIG. 18 is an exploded perspective view of the body shown in FIG. 17 including a flow member and end pieces.
Figure 19:
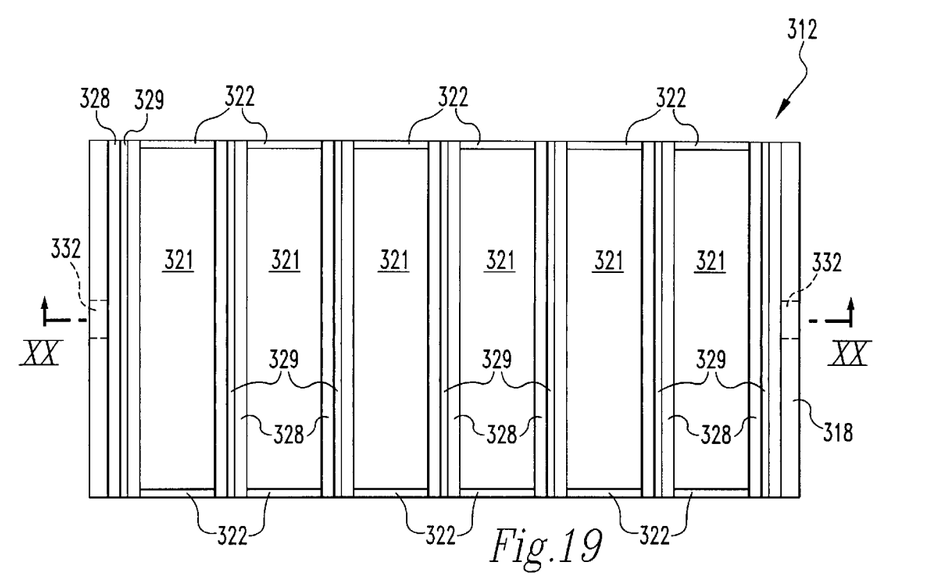
FIG. 19 is a plan view of the flow member shown in FIG. 18.

As shown in FIG. 18, the body 310 preferably includes a multi-sectional flow member 312 and a pair of end pieces 314. The end pieces 314 are fixed to the flow member 312 using screws 316 (FIGS. 16 and 17) or other conventional securing mechanisms. The flow member 312 includes a top surface 318 and a pair of opposing end surfaces 320 (only one being shown). The top surface 318 includes a plurality of flow surfaces 321. A plurality of recesses 322 corresponding in number to the number of flow surfaces 321 is defined in each of the end surfaces 320 and are in fluid communication with the flow surfaces 321. The end pieces 314 each define a plurality of openings 324 and have a top surface 325. Each opening 324 is aligned with one of the recesses 322 and is internally threaded to accept a fitting 326 (FIGS. 16 and 17). When the flow member 312 and the end pieces 314 are assembled as shown in FIG. 17, a plurality of pathways are formed for fluid to flow in the direction shown by arrow A via each set of fittings 326, openings 324, recesses 322 and flow surfaces 321 and out through the corresponding recesses 322, openings 324 and fittings (not shown) in the opposite end of the body 310.

Figure 20:
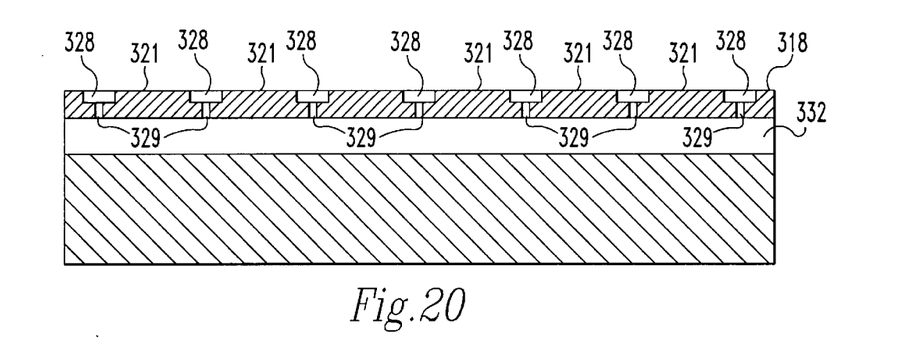
FIG. 20 is a cross-sectional view of the flow member taken along line XX—XX in FIG. 19.

A network of channels 328 having flow slits 329 is defined in the top surface of the body 310. The network of channels 328 is continuous when the body 310 is fully assembled as shown in FIGS. 16 and 17. The flow member 312 has channels 328 which extend parallel to the flow surfaces 321 along the length of the flow member 312. The end pieces 314 each have parallel channels 328 which mate with the channels 328 in the flow member 312 and a channel 328 perpendicular thereto which connects together each of the parallel channels 328. As best shown in FIGS. 18 and 20, an opening 332 is defined in the flow member 312 and extends between opposing sides of the flow member 312. The opening 332 is in fluid communication with the channels 328. A vacuum fitting 334 (FIGS. 16 and 17) is received in one end of the opening 332 and a sealing nut (not shown) is received in the other end of the opening 332.

The gasket 340, similar in material construction to gasket 40 such as molded silicone rubber, is placed over the top surfaces 318 and 325 to cover the network of channels 328. The gasket 340 defines a plurality of apertures 342 at spaced apart locations. When the gasket 340 is seated on the body 310, the apertures 342 are in overlying relation to the flow slits 329 in the channels 328. The gasket 340 also defines a plurality of flow openings 344 corresponding in number to the number of flow surfaces 321 of the flow member 312. Each flow opening 344 overlies one of the flow surfaces 321 of the flow member 312. The cover 350, preferably made of glass or Mylar, is positioned over the gasket 340. When assembled together, each set of a flow surface 321, gasket flow opening 344 and the cover 350 forms a flow chamber in fluid communication at the ends thereof with recesses 322. The thickness of the gasket 340 may be selected to provide a desired volume of fluid flowable through each flow opening 344. The cover 350 may also be clamped to the body 310 using conventional external clamps. The cover 350 may be sized to completely cover the body 310 (as shown in FIG. 16) or be sized to cover only the gasket 340.

In operation, fluid is supplied to the fittings 326 and flows through openings 324 in one end piece 314 and into the recesses 322 on one end of the flow member 312, over the flow surfaces 321 thereby filling the flow openings 344, into the other recesses 322 on the opposite end of the flow member 312 and out through the openings 324 in the other end piece 314. Negative or positive pressure is applied to the vacuum fitting 334 which draws air through the apertures 342 and out through the opening 332 and vacuum fitting 334. The cover 350 is pulled onto the gasket 340 thereby sealing the flow chambers formed at each flow opening 344. Cells may be cultured directly on the flow surfaces 321 or on an underside of the cover 350. Alternatively, a cell culture membrane (not shown), preferably formed from silicone, may be adhered to the underside of the cover 350. The flow rate of fluid applied to each flow chamber may be varied. One or more of the flow chambers may be used at one time. The flow may be continuous in one direction, the flow may be pulsed or the flow may be occasionally or periodically reversed as described above with respect to the assembly 2. In this manner, a variety of stresses may be applied to cultures of cells grown side-by-side in the assembly 302.

An example of the relative dimensions of the components of the assembly 302 are as follows. When the flow member 312 is 6 inches wide and 3.15 inches long, the flow surfaces 321 are 0.65 inch wide. The channels 328 are 0.25 inch wide and the slits 329 are 0.05 inch wide. The recesses 322 extend 1.125 inch downwardly and have a depth of 0.06 inch. The opening 332 is centered 0.15 inch down from the top surface of the flow member 312.

It will be readily appreciated by those skilled in the art that modifications may be made to the invention without departing from the concepts disclosed in the foregoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

I claim:

1. A cell culture assembly for applying shear stress to cells comprising:
   a body having an upper surface defining a first opening therethrough, said body further defining a body passageway;
   a base attached to said body;
   a cell culture membrane fixed between said base and said body; and
   a cover in spaced apart overlying relation to said membrane, whereby said membrane covers said first opening, such that when fluid flows through said body passageway, the fluid passes across said membrane thereby inducing shear stress on cells growing on said membrane or on said cover.

2. The cell culture assembly as claimed in claim 1 wherein said body passageway includes a pair of bores defined in said body on opposing sides of said first opening, wherein each said bore extends between a side of said body and said upper surface.

3. The cell culture assembly as claimed in claim 2 wherein said upper surface defines a pair of second openings on opposing sides of said first opening and each said second opening is in fluid communication with one of said bores.

4. The cell culture assembly as claimed in claim 3 further comprising a gasket positioned between said body upper surface and said cover, said gasket surrounding said first opening and said second openings and being configured to retain fluid flowing out of one said second opening and into the other second opening.

5. The cell culture assembly as claimed in claim 4 wherein said second openings comprise slits.

6. The cell culture assembly as claimed in claim 4 wherein said body further defines a port configured to be connected to a pressure supply and said body upper surface further defines an annular channel in fluid communication with said port, and wherein said gasket overlies said channel.

7. The cell culture assembly as claimed in claim 6 wherein said gasket defines a plurality of holes, said holes overlying said annular channel such that said cover seats on said gasket when negative pressure is applied to said port.

8. The cell culture assembly as claimed in claim 1 wherein said base comprises an annular member defining a chamber and having a wall with a top surface, wherein said membrane seats on said top surface.

9. The cell culture assembly as claimed in claim 8 further comprising an insert received within said chamber, said insert having a support member with a support surface for supporting a portion of said membrane.

10. The cell culture assembly as claimed in claim 9 wherein said wall of said base defines an aperture and said insert defines an insert passageway extending between a side of said insert and said insert support surface, said insert passageway being in fluid communication with said aperture of said base wall such that when a pressure differential is applied to said chamber through said aperture, said membrane is urged against said insert support surface.

11. The cell culture assembly as claimed in claim 10 wherein said insert includes a post spaced apart from said support member thereby defining an annular gap between said post and said support member, said support member defining an opening in fluid communication with said gap.

12. The cell culture assembly as claimed in claim 11 wherein an upper surface of said post is lower than said support surface.

13. The cell culture assembly as claimed in claim 9 wherein an upper surface of the portion of said membrane supported by said support surface is in a plane of said upper surface of said body.

14. A cell culture assembly for applying shear stress to cells comprising:
   a body having a flow surface extending across an upper surface of said body, said body further defining a passageway in fluid communication with said flow surface;
   a cover member covering said flow surface, said flow surface and said cover member thereby defining a flow chamber through which fluid may flow, said flow chamber configured to permit smooth fluid flow therethrough; and
   a cell culture surface positioned on said flow surface or on said cover, whereby cells cultured on said cell culture surface are subject to shear stress when fluid flows through said passageway and said flow chamber,
   wherein said passageway comprises a pair of openings defined in opposing ends of said body and being in fluid communication with said flow surface,
   said body comprises a flow member and a pair of end members attached to opposing ends of said flow member, each said end defining a recess, and
   each said flow surface extends between said recesses and said openings are defined in said end members and are in fluid communication with said recesses.

15. A cell culture assembly for applying shear stress to cells comprising:
   a body having a flow surface extending across an upper surface of said body, said body further defining a passageway in fluid communication with said flow surface;
   a cover member covering said flow surface, said flow surface and said cover member thereby defining a flow chamber through which fluid may flow; and
   a cell culture surface positioned on said flow surface or on said cover, whereby cells cultured on said cell culture surface are subject to shear stress when fluid flows through said passageway and said flow chamber,
   wherein said passageway comprises a pair of openings defined in opposing ends of said body and being in fluid communication with said flow surface;
   said body comprises a flow member and a pair of end members attached to opposing ends of said flow member, said flow member having a pair of opposing ends, each said end defining a recess, and
   an annular channel is defined in an upper surface of said body, said annular channel surrounding said recess flow surface, and wherein said body defines a port in fluid communication with said channel whereby when negative pressure is applied to said port, said cover is urged toward said body.

16. The cell culture assembly as claimed in claim 15, further comprising a gasket defining an opening aligned with said flow surface and defining a plurality of holes therethrough, said gasket being positioned between said body and said cover whereby said opening overlies said flow surface and said holes overlie said channel, such that when negative pressure is applied to said port, said cover sealingly seats on said gasket and said gasket sealingly seats on said body, whereby said flow chamber is defined by said gasket, said cover and said flow surface.

17. The cell culture assembly as claimed in claim 15 wherein said body defines a plurality of said flow surfaces and said channel surrounds each said flow surface defined in said body, said gasket defining a plurality of said openings overlying said flow surfaces, and wherein each said end of said body defines a plurality of openings aligned with said plurality of flow surfaces.

18. The cell culture assembly as claimed in claim 17 wherein said channel is defined in said body between each said flow surface.

19. A cell culture assembly for applying shear stress to cells comprising:

a body having a flow surface extending across an upper surface of said body, said body further defining a passageway in fluid communication with said flow surface, said passageway including a pair of openings in fluid communication with said flow surface;

a cover member covering said flow surface, said flow surface and said cover member thereby defining a flow chamber through which fluid may flow; and a cell culture surface positioned on said flow surface or on said cover, whereby cells cultured on said cell culture surface are subject to shear stress when fluid flows through said passageway and said flow chamber, wherein said body includes a flow member having a pair of opposing ends, and a pair of end members attached to opposing ends of said flow member, each said end defining a recess, each said flow surface extends between said recesses, and said openings are defined in said end members and are in fluid communication with said recesses.

* * * * *